(12) United States Patent
Trieu et al.

(10) Patent No.: US 9,474,559 B2
(45) Date of Patent: Oct. 25, 2016

(54) BONE FASTENER WITH IN VIVO RESORBABLE INSULATING COATING FOR NEURO-MONITORING PURPOSES

(71) Applicant: Warsaw Orthopedic, Inc., Warsaw, IN (US)

(72) Inventors: Hai H Trieu, Cordova, TN (US); Matthew Morrison, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 226 days.

(21) Appl. No.: 14/157,071

(22) Filed: Jan. 16, 2014

(65) Prior Publication Data

US 2015/0196339 A1   Jul. 16, 2015

(51) Int. Cl.
*A61B 17/86* (2006.01)
*A61B 17/70* (2006.01)
*A61B 17/00* (2006.01)

(52) U.S. Cl.
CPC ....... *A61B 17/8625* (2013.01); *A61B 17/7032* (2013.01); *A61B 17/866* (2013.01); *A61B 2017/00004* (2013.01)

(58) Field of Classification Search
CPC ................. A61B 17/8625; A61B 17/8635
See application file for complete search history.

(56) References Cited

U.S. PATENT DOCUMENTS

2008/0221681 A1\* 9/2008 Trieu ................... A61B 17/866
                                                            623/11.11

\* cited by examiner

*Primary Examiner* — David Bates
*Assistant Examiner* — Olivia C Chang (57) ABSTRACT

A bone anchor compatible for use with a neural integrity monitoring systems includes a bone-engaging portion extending between a first end portion and a second end portion. The first end portion includes a resorbable non-electrically conductive polymer defining an insulated region. The second end portion includes a conductive region having reduced electrical resistance relative to the insulated region. The insulated region is contiguous with the conductive region. Methods of use are disclosed.

20 Claims, 4 Drawing Sheets

BONE FASTENER WITH IN VIVO RESORBABLE INSULATING COATING FOR NEURO-MONITORING PURPOSES

TECHNICAL FIELD

The present disclosure generally relates to medical devices for the treatment of bone disorders, and more particularly to a bone fastener compatible for use with a neural integrity monitoring system and method for determining proximity of a bone anchor to neural elements.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatments of these spinal disorders include discectomy, laminectomy, fusion and implantable prosthetics. During surgical treatment, one or more rods may be attached via fasteners, e.g., bone anchors, to the exterior of two or more vertebral members to provide stability to a treated region. However, the fasteners must be placed such that they are sufficiently spaced apart from neural elements to avoid pain. However, placement of fasteners is largely done blindly, and even in the hands of experienced surgeons, the incidence of misplaced fasteners resulting in neurological impairment can be quite high despite the use of surgical inspection and imaging techniques. This disclosure describes an improvement over these prior art technologies.)

SUMMARY

Accordingly, a bone anchor and method for treating a vertebral column is provided. In one particular embodiment, in accordance with the principles of the present disclosure, the bone anchor is compatible for use with a neural integrity monitoring systems and includes a bone-engaging portion extending between a first end portion and a second end portion. The first end portion comprises a resorbable non-electrically conductive polymer defining an insulated region. The second end portion includes a conductive region having reduced electrical resistance relative to the insulated region. The insulated region is contiguous with the conductive region.

In one embodiment, in accordance with the principles of the present disclosure, a bone anchor is provided that is compatible for use with a neural integrity monitoring systems and includes an implant engaging portion configured for engagement with an implant. The bone fastener further includes a bone engaging portion extending from the implant engaging portion. The bone engaging portion comprises a first portion comprising a resorbable non-electrically conductive polymer defining an insulated region and a second portion comprising a conductive region having reduced electrical resistance relative to the insulated region. The bone engaging portion comprises a shank and at least one thread lead extending about the shank. The shank and upper and lower flank surfaces of the thread lead define the insulated region and an outer thread crest of the thread lead define the conductive region.

A method for determining proximity of a bone anchor to neural elements is provided in accordance with the principles of the present disclosure. The method includes the steps of: positioning a bone engaging portion of the bone anchor in bone, the bone engaging portion comprising a first portion comprising a resorbable non-electrically conductive polymer defining an insulated region, the bone engaging portion comprising a second portion comprising a conductive region having reduced electrical resistance relative to the insulated region; delivering a signal to the bone engaging portion; and determining proximity of the bone anchor relative to neuronal elements based upon a patient's response to the signal.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the bone anchor disclosed are discussed in terms of medical devices for the treatment of bone disorders and more particularly, in terms of a bone fastener compatible for use with a neural integrity monitoring system and method for determining proximity of a bone anchor to neural elements. In some embodiments, the bone anchor is formed from a metal, such, as, for example, titanium (Ti), Ti-6Al-4V, Cobalt-Chrome (CoCr) or stainless steel. In some embodiments, the bone anchor is formed from a polymer, such, as, for example, Polyether ether ketone (PEEK), carbon-PEEK, hydroxyapatite (HA) hydroxyapatite-Polyether ether ketone, (HA-PEEK), Polylactide (PLA) or Poly(L-co-D,L-latic add) (PLDLA). In some embodiments, the bone anchor is configured for a variety of applications, such as, for example, spinal fixation, femur fracture stabilization and large joint replacement fixation and may be used at a variety of anatomical locations, such as, for example, pedicle, cervical spine, lumbar spine, sacroiliac joint, hip, knee, shoulder or elbow.

In some embodiments, in accordance with the principles of the present disclosure, an outer surface of the bone fastener or bone screw is coated with a resorbable material, such as, for example, polyesters, polyanhydrides, polyamides, polyurethanes, polyureas, polyethers, polysaccharides, polyamines, polyphosphates, polyphosphonates, polysulfonates, polysulfonamides, polyphosphazenes, silicon oxycarbide, polysiloxane, plasma-polymerized hexamethyldisiloxane, a hydrogel, polylactides or polyglycolides. Specific examples of resorbable polymers include but are not limited to fibrin, collagen, polycaprolactone, poly(glycolic acid), poly(3-hydroxybutric acid), poly(d-lactic acid), poly (dl-lactic add), poly(1-lactic acid) (PLLA), poly(lactide/glycolide) copolymers, poly(hydroxyvalerate), poly(hydroxy-varelate-co-hydroxybutyrate) (PHA), or other PHAs, or other resorbable materials, e.g., protein cell matrices, plant and carbohydrate derivatives (sugars). Resorbable polymers in accordance with the principles of the present disclosure include homopolymers, copolymers or a blend of two or more homopolymers or copolymers. Resorbable polymers in accordance with the principles of the present disclosure can have any molecular architecture and can be linear, branched, hyper-branched or dendritic. In some embodiments, the resorbable polymers are linear or branched.

In some embodiments, the resorbable polymers can be any molecular weight, as long as the material that comprises the resorbable polymer has Young's modulus about 1-300 GPa and/or tensile strength about 20-200 MPa. Resorbable polymers in accordance with the principles of the present disclosure can range from a single repeat unit to about 10 million repeat units. In some embodiments, resorbable polymers in accordance with the principles of the present disclosure have molecular weights of about 10 Daltons to about 100,000,000 Daltons. In some embodiments, resorbable polymers in accordance with the principles of the present disclosure comprise polymer compositions having a range or specific combination of ranges of molecular weights. In some embodiments, resorbable polymers in accordance with the principles of the present disclosure comprise a single polymer, or alternatively, a blend of two or more different polymers. In some embodiments, resorbable polymers in accordance with the principles of the present disclosure linear poly(1-lactic acid) and poly(glycolic acid) having molecular weights of about 10,000 to about 1,000,000 Daltons.

In one embodiment, in accordance with the principles of the present disclosure, a portion of an outer surface of the bone fastener or bone screw is coated with a resorbable polymer that is dielectric or otherwise non-electrically conductive. In some embodiments, the resorbable polymer coating is sufficiently thin so that it is not significantly delaminated and separated from the screw surface during screw insertion into the pedicle. In some embodiments, the coating is made of a resorbable polymer such as, for example, glycerate-3-phosphate, (PGA), polylactide (PLA), poly(lactic-co-glycolic) acid, (PLEA), poly(L-lactide-co-D, L-lactide) (PLDLA), or polycaprolactone. In some embodiments, the coating has a thickness between about 1 nm to about 1 mm. In one embodiment, the thickness of the coating is between about 1 micron to about 250 microns. In some embodiments, resorption time for the coating is between about 1 day and about 10 years. In some embodiments, resorption time for the coating is between about 1 week and about 6 months. In some embodiments, the resorption time is the time it takes for 50% of the coating's original mass to be removed. For example, a coating having a resorption time of 6 months has less than 50% of the coating's original mass after 6 months.

In some embodiments, in accordance with the principles of the present disclosure, an outer surface of the bone fastener or bone screw is coated with a HA-resorbable polymer composite to provide osseoconductivity to the bone fastener. In some embodiments, the HA particles are embedded and distributed throughout the coating to help accelerate degradation and disintegration of the coating, due to its large surface area and hydrophilicity. It is envisioned that the HA may also help to neutralize acidic degradation products of resorbable polymers. In some embodiments, the size of the HA particles used to coat the bone fasteners disclosed herein can vary from 1 nm to 1 mm, preferably between about 100 nm and about 250 microns. In some embodiments, the maximum HA particle diameter is less than that of the final coating thickness. In some embodiments, HA content within the composite coating can be in the range between about 49 and about 1% by volume, preferably between about 70% and about 5%.

In some embodiments, in accordance with the principles of the present disclosure, the HA coating is porous and can readily absorb water or body fluids due to HA's hydrophilicity. Upon rapid fluid absorption, the initially dry and dieletric HA coating becomes semiconductive, which renders it a poor and unreliable insulating coating for neuromonitoring purposes. However, the osseointegration property of HA is desirable for implant fixation purposes. Therefore, in some embodiments, the HA is applied directly to an outer surface of a bone fastener, such as, for example a bone fastener having a shank made from titanium such that the HA will contact the titanium directly. In some embodiments, a resorbable polymer coating is applied on top of the HA coating. That is, the HA coating is applied directly to the outer surface of the bone fastener and the resorbable polymer coating is applied over the HA. It is envisioned that the resorbable polymer coating will seal the porous surface of the HA coating in order to slow down or prevent fluid absorption by the underneath HA coating. Applying a composite laminate coating over the HA coating thus provides a more reliable and improved electrical insulation compared to the HA coating alone.

In some embodiments, in accordance with the principles of the present disclosure, an outer surface of the bone fastener or bone screw is coated with a resorbable polymer and a layer of HA is applied over the polymer coating. This configuration allows fluids to be readily absorbed by the HA coating; however, insulating properties of the overall coating (the combination of the resorbable polymer coating and the HA coating) is still maintained by the resorbable polymer layer underneath the HA coating.

In some embodiments, in accordance with the principles of the present disclosure, an outer surface of the bone fastener or bone screw is coated with a polymer such, as for example, PGA, PLEA, PLDLA, wherein the polymer comprises osseoconductive ceramic particles, such as, for example, particles made of: high crystallinity HA (crystallinity less than about 95%), lower crystallinity HA (ctystalinity greater than about 95%), TCP, HA/TCP and bioactive glass. In some embodiments, the size of the osseoconductive ceramic particles used to coat the bone fasteners disclosed herein can vary from 1 nm to 1 mm, preferably between about 100 nm and about 250 microns. In some embodiments, the maximum osseoconductive ceramic particle diameter is less than that of the final coating thickness. In some embodiments, osseoconductive ceramic particle content within the composite coating can be in the range between about 49 and about 1% by volume, preferably between about 70% and 5%.

In some embodiments, in accordance with the principles of the present disclosure, the resorbable polymer coating comprises a plasticizer that can decrease the flexural modulus of the resorbable polymer. In some embodiments, the plasticizer can influence the morphology of the polymer and can affect the melting temperature and glass transition temperature. In some embodiments, the plasticizer includes small organic and inorganic molecules, oligomers and small molecular weight polymers (those having molecular weight less than about 50,000), highly-branched polymers and dendrimers, such as, for example, ethylene glycol, diethylene glycol, triethylene glycol, oligomers of ethylene glycol, 2-ethylhexanol, isononyl alcohol, isodecyl alcohol, sorbitol, mannitol, trehalose, oligomeric ethers such as oligomers of polyethylene glycol (PEG), including PEG-500, PEG 1000 and PEG-2000 and other biocompatible plasticizers.

In some embodiments, in accordance with the principles of the present disclosure, the resorbable polymer coating comprises a modifier to affect the properties of the polymer and/or the coating. In some embodiments, in accordance with the principles of the present disclosure, the modifier includes a resorbable filler, an antioxidant, colorant, cross-linking agent and/or impact strength modifier.

In some embodiments, in accordance with the principles of the present disclosure, the resorbable polymer coating comprises a biologically active agent or drug. In some embodiments, the agent or drug is introduced into the body lumen as the resorbable polymer coating is resorbed. In some embodiments, the agent or drug includes antiplatelet agents, calcium agonists, calcium antagonists, anticoagulant agents, antimitotic agents, antioxidants, antimetabolites, antithrombotic agents, anti-inflammatory agents, antiproliferative drugs, hypolipidemic drugs and angiogenic factors. In some embodiments, the agent or drug includes glucocorticoids (e.g. dexamethasone, betamethasone), fibrin, heparin, hirudin, tocopherol, angiopeptin, aspirin, ACE inhibitors, growth factors and oligonucleotides. In one embodiment, the resorbable polymer coating comprises one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same. BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a", "an" and "the" include the plural, and reference to a particular numerical value includes at least that particular value, unless the context dearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
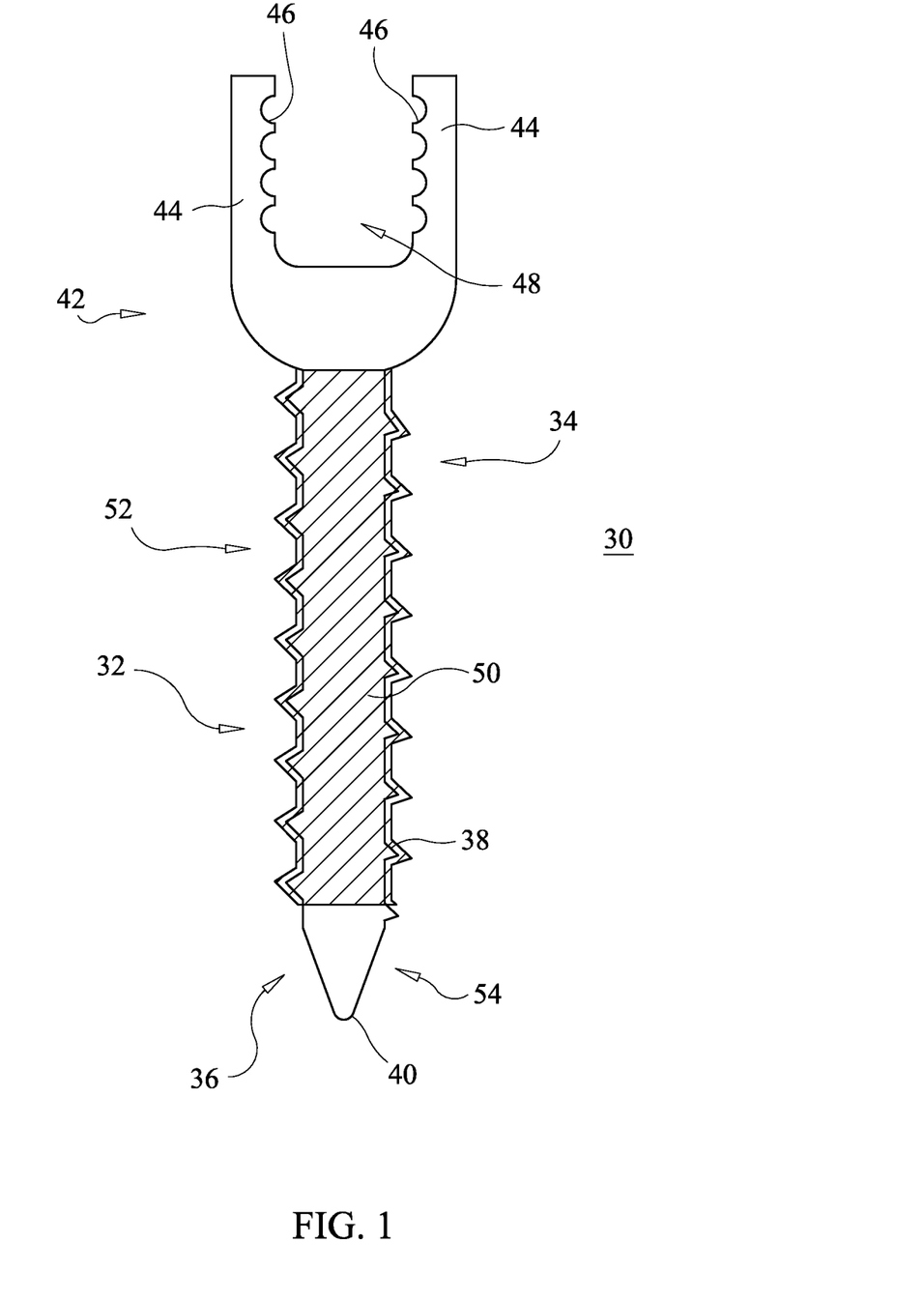
FIG. 1 is a perspective view of one particular embodiment of a bone anchor in accordance with the principles of the present disclosure.
Figure 2:
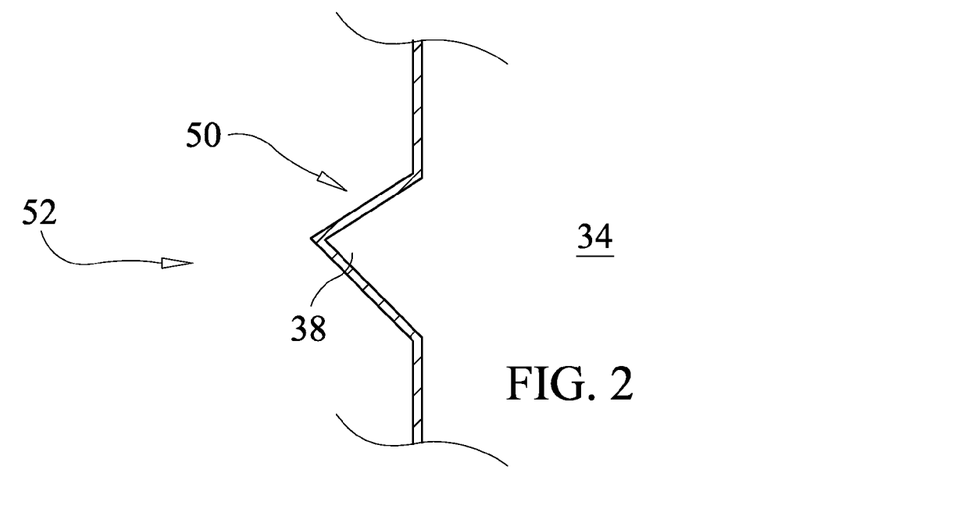
FIG. 2 is an enlarged, detailed view of a portion of the bone anchor shown in FIG. 1.

The following discussion includes a description of surgical system comprising a bone fastener, related components and exemplary methods for treating a vertebral column in accordance with the principles of the present disclosure. Alternate embodiments are also disclosed. Reference will now be made in detail to the exemplary embodiments of the present disclosure, which are illustrated in the accompanying figures. Turning now to FIGS. 1 and 2, there is illustrated components of one embodiment of a bone anchor such as, for example, bone fastener 30, in accordance with the principles of the present disclosure.

The components of the surgical system comprising fastener 30 are fabricated from materials suitable for medical applications, including metals, polymers, ceramics, biocompatible materials and/or their composites, depending on the particular application and/or preference of a medical practitioner. For example, the components of bone 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglyclolide, polytyrosine carbonate, polycaroplaetohe and their combinations. Various components of fastener 30 may have material composites, including the above materials, to achieve various desired characteristics such as strength, rigidity, elasticity, compliance, biomechanical performance, durability and radiolucency or imaging preference. The components of fastener 30, individually or collectively, may also be fabricated from a heterogeneous material such as a combination of two or more of the above-described materials. The components of fastener 30 may be monolithically formed, integrally connected or include fastening elements and/or instruments, as described herein.

Fastener 30 is configured for attachment to bone, such as, for example, vertebrae during surgical treatment of a spinal disorder, examples of which are discussed herein. Fastener 30 includes a shank, such as, for example, a bone-engaging portion 32 extending between a first end portion 34 and a second end portion 36. In some embodiments, portion 32 includes an outer surface having at least one external thread 38 extending outwardly therefrom. In some embodiments, thread 38 is a helical thread. In some embodiments, thread 38 may include a single thread turn or a plurality of discrete threads. In some embodiments, thread 38 extends continuously from portion 34 to portion 36. In some embodiments, thread 38 includes a major diameter and a minor diameter that are constant along the entire length of thread 38. In some embodiments, thread 38 extends along only a part of portion 32 such that at least part of portion 32 is unthreaded. In some embodiments, thread 38 has a single lead. In some embodiments, thread 38 includes more than one lead. In some embodiments, thread 38 is self-tapping. In some embodiments, a tip 40 of portion 36 is sharp and is configured to penetrate tissue, such as, for example, bone. In some embodiments, tip 40 is blunt and/or rounded. In some embodiments, other engaging structures may be located on portion 32, such as, for example, a nail configuration, barbs, expanding elements, raised elements and/or spikes to facilitate engagement of portion 32 with tissue, such as, for example, bone.

In some embodiments, portion 32 has a cylindrical cross sectional configuration. In some embodiments, all or only a part of portion 32 may have alternate cross section configurations, such as, for example, oval, oblong, triangular, square, polygonal, irregular, uniform, non-uniform, offset, staggered, undulating, arcuate, variable and/or tapered. In some embodiments, the outer surface of portion 32 may include one or a plurality of openings. In some embodiments, all or only a portion of the outer surface of portion 32 may have alternate surface configurations to enhance fixation with tissue such as, for example, rough, arcuate, undulating, mesh, porous, semi-porous, dimpled and/or textured according to the requirements of a particular application. In some embodiments, all or only a part of portion 32 may be cannulated.

In some embodiments, portion 32 comprises a conductive material. In some embodiments, portion 32 comprises a non-conductive material. In some embodiments, portion 32 comprises a metal, such as, for example, Ti, Ti-6Al-4V, CoCr, stainless steel, or a combination thereof. In some embodiments, portion 32 comprises a polymer, such as, for example, PEEK, carbon-PEEK, HA-PEEK, PLA, PLDLA, or a combination thereof. It is envisioned that the design, size and shape of fastener 30 may be adapted according to a particular application, such as, for example, spinal fixation, femur fracture stabilization, or large joint replacement fixation and/or according to the anatomic location in which fastener 30 is to be implanted such as, for example, a pedicle, cervical spine, lumbar spine, sacroiliac joint, hip, knee, shoulder or elbow, as would be apparent to one of ordinary skill in the art.

Fastener 30 includes a head 42 connected with portion 32. Head 32 includes a pair of spaced apart arms 44. Inner surfaces 46 of arms 44 define a U-shaped passageway 48 therebetween configured for disposal of a connecting element such as, for example, a vertebral rod. In some embodiments, at least one of surfaces 46 includes an internal thread form configured to engage an external thread form of a retaining element, such as, for example, a set screw to fix a vertebral rod relative to head 42. In some embodiments, portion 32 is rotatable relative to head 42 such that bone fastener 30 is multi-axial. In some embodiments, portion 32 is fixed relative to head 42 such that bone fastener is mono-axial. In some embodiments, portion 32 and head 42 are monolithic. In some embodiments, passageway 48 may have a cross sectional configuration which is round or circular, oval, oblong, square, rectangular, polygonal, irregular, uniform, non-uniform, consistent or variable, according to the requirements of the particular application. That is, in some embodiments, passageway 48 is configured to have an open top (e.g. embodiments where passageway 48 is U-shaped) such that a vertebral rod can be top-loaded into passageway 48 and in other embodiments, passageway 48 is configured to have an closed top (e.g. embodiments where passageway 48 has a circular cross sectional configuration) such that a vertebral rod must be side-loaded into passageway 48.

Portion 34 comprises a polymer 50 defining an insulated region 52 of fastener 30 and portion 36 includes a conductive region 54 having reduced electrical resistance relative to region 52. Region 54 is not coated with polymer 50 such that the outer surface of portion 32 is exposed at region 54. That is, region 54 is free of polymer 50 and/or any other coating applied to the outer surface of portion 32 to reduce the conductivity of region 54. In some embodiments, regions 52, 54 are each coated with polymer 50, with region 52 having a thicker coating of polymer 50 than region 54.

Region 54 exhibits a higher electrical conductance value relative to region 52. In other words, region 54 exhibits less electrical resistance relative to polymer 50 on region 52 to establish a conductive pathway between fastener 30 and the adjacent neural elements or nerves to facilitate operation of a nerve monitoring system. Indeed, polymer 50 acts as an insulator and/or interferes with or significantly weakens a conductive electrical path between portion 32 adjacent tissue, such as, for example, bone, which is necessary for proper operation of a neural integrity monitoring system. In particular, a neural integrity monitoring system directs a conductive electrical current path between portion 32 and adjacent neural elements or nerves to provide an indication to the neural integrity monitoring system corresponding to the presence of a neural element so that corrective action can then be taken by the surgeon based on this indication. Polymer 50 is intended to prevent contact between a surface of fastener 30 and surrounding body fluids and/or tissue in order to prevent shunting tissue during a neural integrity monitoring procedure. Further details regarding neural integrity monitoring systems that may be used with the fasteners of the present disclosure, such as, for example, fastener 30, are described in U.S. patent application Ser. No. 13/007,207 by Jerome Nayet, et al. filed Jan. 14, 2011, the contents of which are incorporated by reference herein, in it is entirety.

In some embodiments, region 52 is contiguous with region 54. In some embodiments, region 52 is spaced apart from region 54 by a third region having electrical resistance that differs from each of regions 52, 54. In some embodiments, the third region is defined by a material applied to the outer surface of portion 32, such as, for example, an insulating material, a conductive material or a combination thereof.

In some embodiments, polymer 50 is biocompatible and osteocompatible to avoid adversely affecting osseointegration of fastener 30 which would result in poor long-term fixation and stability. In some embodiments, polymer 50 is resorbable to promote the normal osseointegration of the outer surface of portion 32 once polymer 50 is resorbed. In some embodiments, polymer 50 is dielectric or otherwise non-electrically conductive. In some embodiments, polymer 50 is resorbable and non-electrically conductive. In some embodiments, polymer 50 includes one or more polymers configured to be resorbed within about 1 day to about 10 years. In some embodiments, polymer 50 includes one or more polymers configured to be resorbed within about 1 day to about 1 year. In some embodiments, polymer 50 is configured to be resorbed between about 1 week and about 12 months. In some embodiments, polymer 50 is configured to be resorbed between 1 week and 6 months. In some embodiments, polymer 50 is configured to be resorbed between 1 week and 2 months.

In some embodiments, polymer 50 is applied to portion 32 by dip-coating, spray-coating, physical vapor deposition or chemical deposition. It is envisioned that polymer 50 can be applied to any part of portion 32. In some embodiments, polymer 50 covers about 80% to about 90% of portion 32. In some embodiments, polymer 50 is applied to portion 32 such that polymer 50 is spaced apart from tip 40. As would be appreciated by those skilled in the art, tip 40 is typically one of the first portions of fastener 30 that makes contact with or is positioned closest in proximity to neural elements or nerves when fastener 30 is driven into bone. Accordingly, a conductive electrical current path between fastener 30 and the adjacent neural elements or nerves may be maintained via providing a conductive surface at tip 40, thereby facilitating proper operation of a neural integrity or nerve monitoring system to accurately monitor and detect neural elements during or subsequent to anchoring of the portion 32 in bone. In some embodiments, polymer 50 is between about 1 mm and about 10 mm from tip 40. In some embodiments, polymer 50 extends continuously from a portion adjacent tip 40 to a portion adjacent head 42 and extends about the circumference of portion 32. That is, polymer 50 coats both the lead or root and the crest of thread 38 as well as grooves between thread 38. In some embodiments, region 52 is defined by one or more strips of polymer 50 that extend parallel to an axis defined by portion 32. In some embodiments, region 52 is defined by one or more strips of polymer 50 that extend perpendicular to the axis defined by portion 32.

In some embodiments, polymer 50 is applied to portion 32 such that polymer 50 is spaced apart from head 42. In some embodiments, polymer 50 is positioned between about 5 mm and 20 mm from head 42. In some embodiments, polymer 50 extends continuously about a circumference of portion 32 such that polymer 50 forms a ring about portion 32. It is envisioned that the ring formed by the polymer may have a width of up to about 5 mm. In some embodiments, polymer 50 extends about only a portion of the circumference of portion 32. In such embodiments, it is envisioned that polymer 50 has a width extending perpendicular to the axis defined by portion 32 that is greater than about 1 mm. In some embodiments, an uncoated portion of fastener 30 defines a ring. It is envisioned that the ring defined by a lack of polymer may have a width of up to about 5 mm. In some embodiments, fastener 30 includes a coated portion directly below head 42 and an uncoated tip 40. In addition in some embodiments fastener 30 includes an uncoated portion directly below the coated portion directly below head 42 that defines a ring and a coated portion between the ring and uncoated tip 40. This configuration allows fastener 30 to be implanted into bone, such as, for example a vertebra, such that an electrical current can flow through tip 40 to detect neuronal elements adjacent fastener 30 as fastener 30 is provisionally implanted into the bone. After fastener 30 is fully implanted into the pedicle of the vertebra, for example, the electrical current can flow through the ring to detect neuronal elements adjacent fastener 30 and define positioning of the fastener 30 when in its final location.

Figure 3:
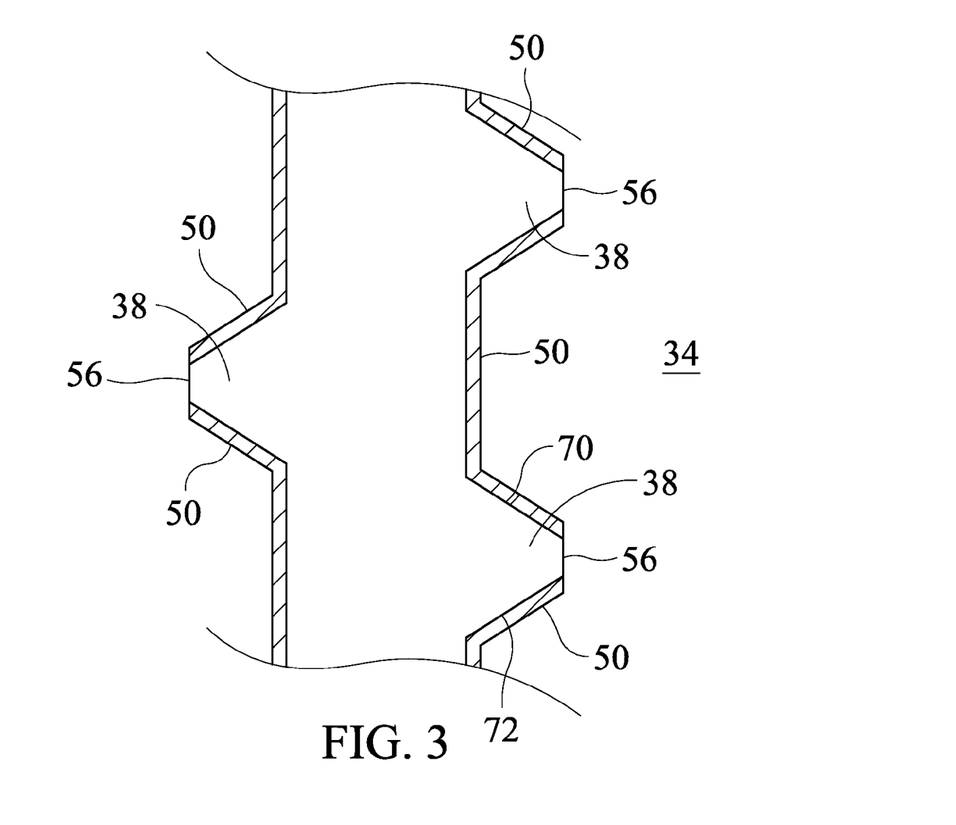
FIG. 3 is an enlarged, detailed view of a portion of one particular embodiment of bone anchor in accordance with the principles of the present disclosure.

In some embodiments, the crest of thread 38 includes an outer crest surface or edge 56 that defines region 54. That is, edge 56 is not coated with polymer 50 and parts of portion 32 adjacent edge 56 (including a root or lead of thread 38) are coated with polymer to define region 52. In particular, opposing upper and lower flank surfaces 70, 72 of thread 38 are coated with polymer and are included in region 52, while edge 56 is not coated with polymer 50. As would be appreciated by those skilled in the art, edge 56 is typically one of the first portions of the fastener 30 that makes contact with or is positioned closest in proximity to neural elements or nerves when fastener 30 is driven into bone. Accordingly, a conductive electrical current path between fastener 30 and the adjacent neural elements or nerves may be maintained via providing a conductive surface along edge 56, thereby facilitating proper operation of a neural integrity or nerve monitoring system to accurately monitor and detect neural elements during or subsequent to anchoring of portion 32 in bone.

Figure 4:
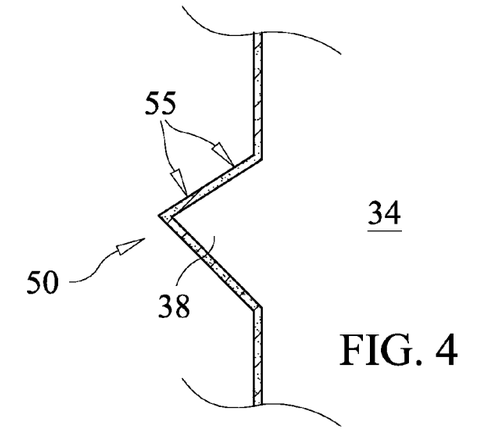
FIG. 4 is an enlarged, detailed view of a portion of one particular embodiment of a bone anchor in accordance with the principles of the present disclosure.

In some embodiments, such as that shown in FIG. 4, polymer 50 comprises hydroxyapatite (HA) 55 added thereto for osseoconductivity purposes. It is also envisioned that adding HA 55 to polymer 50 will accelerate degradation and disintegration of polymer 50 due to the large surface area and hydrophilicity of HA 55 and/or will help to neutralize acidic degradation products in polymer 50. In some embodiments, particles of HA 55 embedded and distributed throughout polymer 50. In some embodiments, the particles of HA 55 are uniformly distributed throughout polymer 50 in a noncontiguous format. In some embodiments, the particles of HA 55 are randomly distributed in polymer 50. In some embodiment, at least one of the particles of HA 55 extend through an outer surface of polymer 50. In some embodiments, none of the particles of HA 55 extend through the outer surface of polymer 50.

In some embodiments, HA particles 55 can vary in size from about 1 nm to about 1 mm. In some embodiments. HA particles 55 can vary in size from about 100 nm to about 250 μm. In some embodiments. HA particles 55 have a maximum diameter that is less than that of the final thickness of polymer 50. In some embodiments, HA content within the coating that includes polymer 50 and HA particles 55 is between about 49% and about 1% by volume. In some embodiments, HA content within the coating that includes polymer 50 and HA particles 55 is between about 70% and about 5%. In some embodiments, HA particles 55 are be replaced with osseoconductive ceramic particles such as, for example particles made of high crystallinity HA (crystallinity greater than about 95%), lower crystallinity HA (crystallinity less than about 95%), HA/TCP, bioactive glass, or a combination thereof.

In some embodiments, polymer 50 comprises silver added thereto for antimicrobial purposes. It is envisioned that polymer 50 may include up to about 50% silver by volume. It I also envisioned that the silver is dispersed throughout the polymer in a noncontiguous arrangement so as to maintain the non-conductivity of polymer 50. In some embodiments, polymer 50 includes about 0.1% to about 10% silver by volume. It is envisioned that polymer 50 may include silver in addition to any of the other materials discussed herein, such as, for example, HA.

In some embodiments, the thickness of polymer 50 applied to the outer surface of portion 34 is sufficiently thin so that polymer 50 is not separated from the outer surface of portion 32 during insertion of fastener 30 into a bone, such as, for example, a pedicle. In some embodiments, polymer 50 has a thickness between about 1 nm and about 1 mm. In some embodiments, polymer 50 has a thickness between 1 nm and 1 mm. In some embodiments, polymer 50 has a thickness between 1 μm and 250 μm.

In some embodiments, polymer 50 comprises one or more of polyester, polyanhydride, polyimide, polyurethane, polyurea, polyether, polysaccharides, polyamine, polyphosphate, polyphosphonate, polysulfonate, polysulfonamide, polyphosphazene, silicon oxycarbide, polysiloxane, plasma-polymerized hexamethyldisiloxane, hydrogel, polylactide, polyglycolide, or combinations thereof. In some embodiments, polymer 50 comprises one or more of PGA, PLGA, PLDLA, fibrin, collagen, polycaprolactone, poly(glycolic acid), poly(3-hydroxybutric add), poly(d-lactic acid), poly(dl-lactic acid), poly(l-lactic acid) (PLLA), poly(lactide/glycolide) copolymers, poly(hydroxyvalerate), poly(hydroxy-varelate-co-hydroxybutyrate), other PHAs, or other resorbable materials such as, for example, protein cell matrices, plant and carbohydrate derivatives (sugars). In some embodiments, polymer 50 comprises one or more of homopolymers, copolymers or a blend of two or more homopolymers or copolymers. In some embodiments, polymer 50 is linear, branched, hyper-branched or dendritic.

In some embodiments, polymer 50 can range from a single repeat unit to about 10 million repeat units such that polymer 50 has a molecular weight of about 10 Daltons to about 100,000,000 Daltons. In some embodiments, polymer 50 comprises polymer compositions having a range or specific combination of ranges of molecular weights. In some embodiments, polymer 50 comprises a single polymer. In some embodiments, polymer 50 comprises a blend of two or more different polymers. In some embodiments, polymer 50 comprises linear poly(l-lactic acid) and poly(glycolic acid) having molecular weights of about 10,000 to about 1,000,000 Daltons. In some embodiments, the molecular weight of polymer 50 is selected to impart polymer 50 with a Young's modulus of about 1 GPa to about 300 GPa and/or a tensile strength of about 20 MPa to about 200 MPa.

In some embodiments, polymer 50 comprises a plasticizer or other material that can decrease the flexural modulus of polymer 50, can influence the morphology of polymer 50 and/or can affect the melting temperature and glass transition temperature polymer 50. Examples of plasticizers suitable for use with polymer 50 include, but are not limited to, small organic and inorganic molecules, oligomers and small molecular weight polymers (those having molecular weight less than about 50,000), highly-branched polymers and dendrimers, ethylene glycol, diethylene glycol, triethylene glycol, oligomers of ethylene glycol, 2-ethylhexanol, isononyl alcohol, isodecyl alcohol, sorbitol, mannitol, oligomeric ethers such as oligomers of polyethylene glycol, including PEG-500, PEG 1000 and PEG-2000 and other biocompatible plasticizers.

In some embodiments, polymer 50 comprises a modifier or other material added to polymer 50 to affect the ability of polymer 50 to coat portion 32. Examples of suitable modifiers for use with polymer 50 include, but are not limited to resorbable fillers, antioxidants, colorants, crosslinking agents and impact strength modifiers.

In some embodiments, polymer 50 comprises a biologically active agent or drug that will be introduced into the body of a patient as polymer 50 is resorbed. Agents or drugs suitable for use with polymer 50 include, but are not limited to, antiplatelet agents, calcium agonists, calcium antagonists, anticoagulant agents, antimitotic agents, antioxidants, antimetabolites, antithrombotic agents, anti-inflammatory agents, antiproliferative drugs, hypolipidemic drugs, angiogenic factors, glucocorticoids (e.g. dexamethasone, betamethasone), fibrin, heparin, hirudin, tocopherol, angiopeptin, aspirin, ACE inhibitors, growth factors and oligonucleotides. In one embodiment, the agent comprises one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same. BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In assembly, operation and use, fastener 30 is employed with a surgical procedure for treatment of a spinal disorder affecting a section of a spine of a patient, as discussed herein. Fastener 30 may also be employed with other surgical procedures. For example, fastener 30 may be employed with a surgical procedure for treatment of a condition or injury of an affected section of the spine inducting one or more vertebrae. It is contemplated that fastener 30 is attached to vertebrae for fusion and/or dynamic stabilization applications of the affected section of the spine to facilitate healing and therapeutic treatment.

Figure 5:
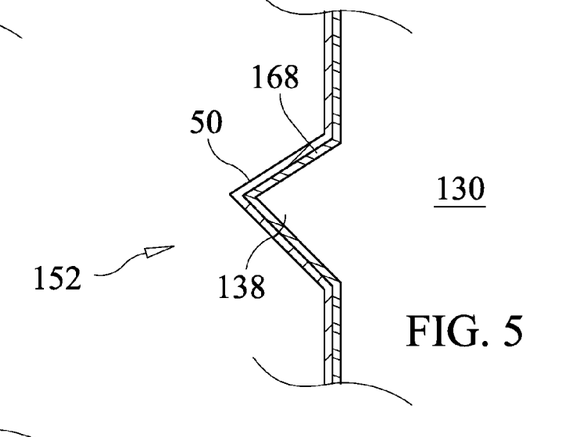
FIG. 5 is an enlarged, detailed view of a portion of one particular embodiment of a bone anchor in accordance with the principles of the present disclosure.

In one embodiment in accordance with the principles of the present disclosure, shown in FIG. 5, a fastener 130 has a configuration similar to that of fastener 30 and includes a thread 138 similar to thread 38 and an insulated region 152 similar to region 52. An outer surface of fastener 130 is coated with a layer 168 consisting essentially of hydroxyapatite (HA). That is, layer 168 directly engages the outer surface of fastener 130 for the purposes of implant fixation. However, HA is typically porous and can readily absorb water or body fluids due to HA's hydrophilicity. Therefore, upon rapid fluid absorption, the initially dry and dieletric HA coating becomes semiconductive, which renders it a generally poor and unreliable insulating coating for neuro-monitoring purposes. Therefore, fastener 130 has a polymer, such as, for example, polymer 50 applied directly on top of layer 168. That is, polymer 50 is spaced apart from the outer surface of fastener 130 by layer 168. The layer of polymer 50 coating layer 168 is expected to seal the porous surface of the HA coating in order to slow down or prevent fluid absorption by layer 168.

Figure 6:
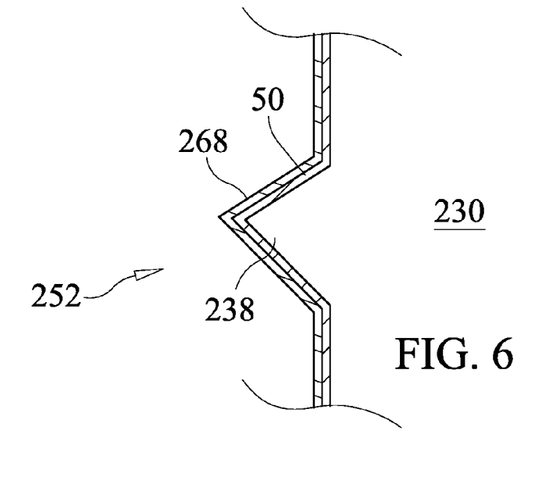
FIG. 6 is an enlarged, detailed view of a portion of one particular embodiment of a bone anchor in accordance with the principles of the present disclosure.

In one embodiment in accordance with the principles of the present disclosure, shown in FIG. 6, a fastener 230 has a configuration similar to that of fasteners 30, 130 and includes a thread 238 similar to threads 38, 138 and an insulated region 252 similar to regions 52, 152. An outer surface of fastener 230 is coated with a polymer, such as, for example, polymer 50. That is, polymer 50 directly engages the outer surface of fastener 230. A layer 268 similar to layer 168 that consists essentially of hydroxyapatite (HA) directly engages polymer 50 such that layer 268 is spaced apart from the outer surface of fastener 230 by polymer 50. While HA is known to absorb fluids, the insulating properties of the combination of polymer 50 and layer 268 are maintained.

In use, to treat the affected section of the spine, a medical practitioner obtains access to a surgical site including one or more vertebrae in any appropriate manner, such as through incision and retraction of tissues. It is envisioned that fastener 30 may be used in any existing surgical method or technique including open surgery, mini-open surgery, minimally invasive surgery and percutaneous surgical implantation, whereby one or more vertebrae are accessed through a micro-incision, or sleeve that provides a protected passageway to the area. Once access to the surgical site is obtained, the particular surgical procedure is performed for treating the spinal disorder. Fastener 30 is then employed to augment the surgical treatment. The components of fastener 30 can be delivered or implanted as a pre-assembled device or can be assembled in situ.

Figure 7:
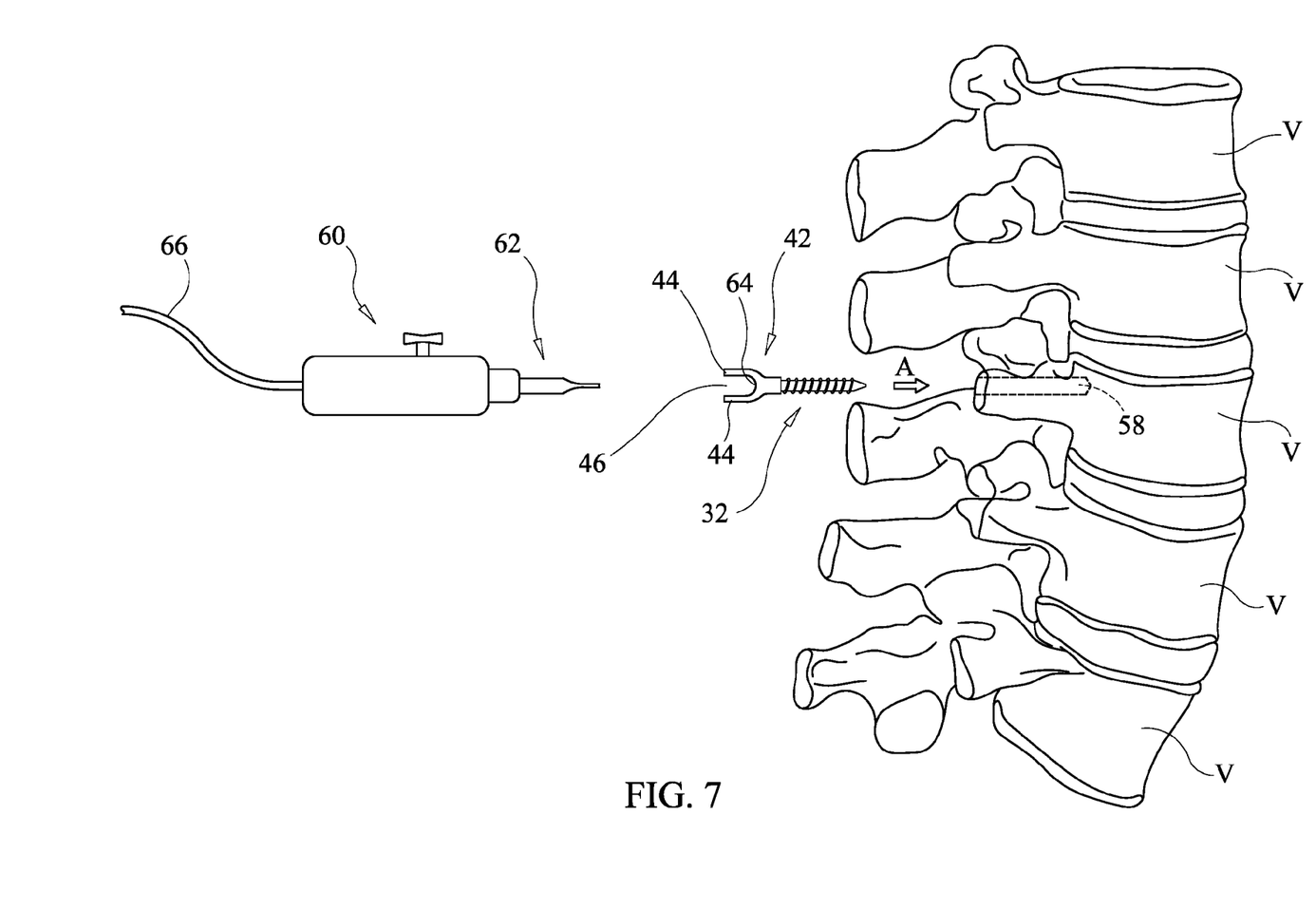
FIG. 7 is a diagrammatic side view of the bone anchor shown in FIG. 1 and a surgical tool relative to a section of a spinal column for use in association with a neural integrity monitoring system.

A pilot hole 58 may be formed in one of vertebrae V as shown in FIG. 7 using a boring instrument. Fastener 30 may then be aligned with hole 58 and rotated relative to a respective one of vertebrae V using a driving instrument, such as, for example, surgical tool 60 comprising a driver portion 62 to fix fastener 30 relative to a respective one of vertebrae V. That is, portion 62 is positioned relative to fastener 30 such that portion 62 becomes provisionally fixed relative to portion 32 and/or head 42. In embodiments where portion 32 is rotatable relative to head 42 (fastener 30 is multi-axial), it is envisioned that portion 62 may inserted into a tool engaging recess extending into a proximal end surface of portion 32 to provisionally fix portion 62 relative to portion 32. In embodiments where portion 32 is fixed relative to head 42 (fastener 30 is mono-axial), it is envisioned that portion 62 may inserted into a tool engaging recess 64 extending into head 42 to provisionally fix portion 62 relative to head 42. In some embodiments, portion 62 and the tool engaging recess in a respective one of portion 32 and head 42 have complimentary cross-sectional configurations such as, for example, tri-flat, square, hexagonal, polygonal, star, groove, Phillips, cruciate, slot or hexalobe. In some embodiments, portion 62 is non-insulated to conductively couple portion 62 to the portion 32 or head 42 to allow conductive transfer of an electrical signal from the adjacent bone tissue to portion 32 for monitoring and detection of nerve proximity.

Portion 62 rotates relative to a respective one of vertebrae V in a first direction, such as, for example, clockwise or counterclockwise to move fastener 30 within hole 58 in the direction shown by arrow A. It is envisioned that fastener 32 may be inserted into a respective one of vertebrae V without hole 58, especially where thread 38 is self-tapping. In such embodiments, tip 40 is positioned to engage an outer surface of a respective one of vertebrae V. Portion 62 engages portion 32 and/or head 42 in the manner discussed above. Fastener 30 is then rotated in the first direction using tool 60 to move fastener 30 within the respective one of vertebrae V in the direction shown by arrow A.

Tool 60 is coupled to a link 66 of a nerve monitoring system, such as, for example the NIM-Spine® System marketed by Medtronic, Inc. The nerve monitoring system is operable to detect impingement, interference, and encroachment or close proximity between the portion 32 and a neural element during and after insertion of portion 32 into the respective one of vertebrae V. In particular, as portion 32 is being inserted into the respective one of vertebrae V, the nerve monitoring system supplies tool 60 with an electrical signal that is used to locate neural elements in contact with or proximate to portion 32. An electrical lead is positioned in electrical communication with portion 62 for coupling with a source of electrical current, either separately from or part of link 52. In some embodiments, an electrical signal or current is delivered to portion 62 to provide monitoring and detection of neural elements. Portion 62 carries an electrical signal that provides an indication of the proximity of neural elements in or adjacent to the bone tissue relative to portion 32. The electrical signal or current is delivered from portion 62 and through the head 42 to provide an indication of the proximity of neural elements in the bone tissue relative to the portion 32 during and after implantation of the portion 32 into the respective one of vertebrae V.

In some embodiments, the electric signal provides electrical stimulation to the tissue surrounding fastener 30, and the patient's response to the nerve stimulation is monitored to determine whether a neural element threshold level has been reached. The threshold level can correspond to, for example, an indication of the presence of a neural element and/or its proximity relative to fastener 30. In another embodiment, when portion 32 is positioned near or proximate a neural element, the presence of the neural element creates an electrical current path for conduction of an electrical signal. The current path provides an indication to the nerve monitoring system corresponding to the presence of the neural element, and corrective action can then be taken by the surgeon based on this indication. In other words, detection of the neural element threshold occurs as a function of the electrical signal at portion 32, thereby inducing a reaction in the patient or a particular reading of the threshold level.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto

What is claimed is:

1. A bone anchor compatible for use with a neural integrity monitoring system, the bone anchor comprising:
    a bone-engaging portion extending between a first end portion and a second end portion, the bone anchor comprising a thread that extends across the first end portion, wherein the bone anchor comprises a coating that extends along an entire length of the thread and covers upper and lower flank surfaces of the thread without covering an outer crest surface of the thread, the coating comprising a resorbable non-electrically conductive polymer, the coating defining an insulated region of the bone anchor, the second end portion including a conductive region of the bone anchor, the conductive region having reduced electrical resistance relative to the insulated region, the insulated region being contiguous with the conductive region.

2. A bone anchor as recited in claim 1, wherein the conductive region is free of the resorbable polymer.

3. A bone anchor as recited in claim 1, wherein the resorbable polymer comprises an agent to promote osseointegration.

4. A bone anchor as recited in claim 3, wherein the agent comprises hydroxyapatite.

5. A bone anchor as recited in claim 4, wherein the hydroxyapatite is non-contiguously embedded and distributed throughout the resorbable polymer.

6. A bone anchor s recited in claim 4, wherein the resorbable polymer comprises between about 1% to about 70% hydroxyapatite by volume.

7. A bone anchor as recited in claim 1, further comprising an agent to promote osseointegration engaging an outer surface of the first end portion, wherein the resorbable polymer is applied over the agent such that the resorbable polymer is spaced apart from the outer surface of the first end portion by the agent.

8. A bone anchor as recited in claim 7, wherein the agent comprises hydroxyapatite and the resorbable polymer is free of hydroxyapatite.

9. A bone anchor as recited in claim 1, wherein the resorbable polymer directly contacts an outer surface of the first end portion and the bone anchor further comprises an agent to promote osseointegration applied over the resorbable polymer such that the agent is spaced apart from the outer surface of the first end portion by the resorbable polymer.

10. A bone anchor as recited in claim 9, wherein the agent comprises hydroxyapatite and the resorbable polymer is free of hydroxyapatite.

11. A bone anchor as recited in claim 1, wherein the resorbable polymer has a Young's modulus of about 1 to about 300 GPa.

12. A bone anchor as recited in claim 1, wherein the bone anchor comprises a head that is free of threads.

13. A bone anchor as recited in claim 1, wherein the polymer comprises polyesters, polyanhydrides, polyamides, polyurethanes, polyureas, polyphosphates, polyphosphonates, polysulfonates, polysulfonamides, polyphosphazenes, silicon oxycarbide, polysiloxane, plasma-polymerized hexamethyldisiloxane, or a combination thereof.

14. A bone anchor as recited in claim 1, wherein the resorbable polymer comprises silver.

15. A bone anchor compatible for use with a neural integrity monitoring system, the bone anchor comprising:
    a bone-engaging portion extending between a first end portion and a second end portion, the first end portion comprising a thread that extends continuously from a proximal end of the first end portion to an opposite distal end of the first end portion, wherein the thread comprises a resorbable non-electrically conductive polymer that coats upper and lower flank surfaces of the thread along an entire length of the thread without coating an outer crest surface of the thread such that the first end portion defines an insulated region of the bone anchor, the second end portion defining a conductive region of the bone anchor, the conductive region having reduced electrical resistance relative to the insulated region,
    wherein the resorbable polymer consists of a material selected from a group consisting of polyesters, polyanhydrides, polyamides, polyurethanes, polyureas, polyethers, polysaccharides, polyamines, polyphosphates, polyphosphonates, polysulfonates, polysulfonamides, polyphosphazenes, silicon oxycarbide, polysiloxane, plasma-polymerized hexamethyldisiloxane, a hydrogel, polylactides and polyglycolides.

16. A bone anchor as recited in claim 15, further comprising a composite laminate coating that is applied over the resorbable polymer.

17. A bone anchor as recited in claim 15, wherein the bone anchor is formed from a polymer.

18. A bone anchor as recited in claim 15, wherein the bone anchor comprises a head comprising spaced apart arms that define a U-shaped passageway therebetween configured for disposal of a vertebral rod.

19. A bone anchor compatible for use with a neural integrity monitoring system, the bone anchor comprising:
    a bone-engaging portion extending between a first end portion and a second end portion, the bone anchor comprising a thread that extends across the first end portion, wherein the bone anchor comprises a resorbable non-electrically conductive polymer that coats adjacent upper and lower flank surfaces of the thread that are spaced apart from one another by an outer crest surface of the thread without covering the outer crest surface such that the flank surfaces define an insulated region of the bone anchor, the bone anchor comprising a composite laminate coating that is applied over the resorbable polymer, the second end portion and the outer crest defining a conductive region of the bone anchor, the conductive region having reduced electrical resistance relative to the insulated region.

20. A bone anchor as recited in claim 19, wherein the resorbable polymer comprises hydroxyapatite.

\* \* \* \* \*

UNITED STATES PATENT AND TRADEMARK OFFICE
CERTIFICATE OF CORRECTION

PATENT NO. : 9,474,559 B2
APPLICATION NO. : 14/157071
DATED : October 25, 2016
INVENTOR(S) : Trieu et al.

It is certified that error appears in the above-identified patent and that said Letters Patent is hereby corrected as shown below:

On the Title Page

Item (72), Column 1, Line 1, delete "Hai H" and insert -- Hai H. --, therefor.

In the Specification

Column 1, Line 38, delete "technologies.)" and insert -- technologies. --, therefor.

Column 2, Line 29, delete "of" and insert -- of a --, therefor.

Column 2, Line 61, delete "latic add)" and insert -- lactic acid) --, therefor.

Column 3, Line 14, delete "add), poly(1-lactic acid)" and insert -- acid), poly(l-lactic acid) --, therefor.

Column 3, Line 45, delete "poly(1-lactic acid)" and insert -- poly(l-lactic acid) --, therefor.

Column 3, Line 58, delete "(PLEA)," and insert -- (PLGA), --, therefor.

Column 4, Line 56, delete "PLEA," and insert -- PLGA, --, therefor.

Column 4, Lines 59-60, delete "(ctystalinity" and insert -- (crystalinity --, therefor.

Column 6, Line 30, delete "dearly" and insert -- clearly --, therefor.

Column 8, Line 53, delete "Head 32" and insert -- Head 42 --, therefor.

Column 11, Line 34, delete "embodiments." and insert -- embodiments, --, therefor.

Column 11, Line 36, delete "embodiments." and insert -- embodiments, --, therefor.

Signed and Sealed this
Twenty-fourth Day of January, 2017

Michelle K. Lee
*Director of the United States Patent and Trademark Office*

CERTIFICATE OF CORRECTION (continued)
U.S. Pat. No. 9,474,559 B2

Column 11, Line 52, delete "It I" and insert -- It is --, therefor.

Column 12, Line 2, delete "polyimide," and insert -- polyamide, --, therefor.

Column 12, Line 10, delete "add)," and insert -- acid), --, therefor.

Column 13, Line 28, delete "inducting" and insert -- including --, therefor.

Column 13, Line 33, delete "embodiment" and insert -- embodiment, --, therefor.

Column 13, Line 53, delete "embodiment" and insert -- embodiment, --, therefor.

Column 14, Line 44, delete "fastener 32" and insert -- fastener 30 --, therefor.

Column 14, Line 66, delete "link 52." and insert -- link 66. --, therefor.

In the Claims

Column 15, Line 62, Claim 6, delete "anchor s" and insert -- anchor as --, therefor.